(12) United States Patent
Heimgartner

(10) Patent No.: US 6,688,933 B1
(45) Date of Patent: Feb. 10, 2004

(54) METHOD FOR PRODUCING A COMPONENT AND CORRESPONDING COMPONENT

(75) Inventor: Rudolf Heimgartner, Obertraubling (DE)

(73) Assignee: Osram Opto Semiconductors GmbH & Co. oHG, Regensburg (DE)

( * ) Notice: Subject to any disclaimer, the term of this patent is extended or adjusted under 35 U.S.C. 154(b) by 0 days.

(21) Appl. No.: 09/857,252
(22) PCT Filed: Sep. 24, 1999
(86) PCT No.: PCT/DE99/03083
§ 371 (c)(1), (2), (4) Date: Jan. 14, 2002
(87) PCT Pub. No.: WO00/19397
PCT Pub. Date: Apr. 6, 2000

(30) Foreign Application Priority Data

Sep. 30, 1998 (DE) ............................................ 198 45 075

(51) Int. Cl.[7] .................................................. H01G 9/32
(52) U.S. Cl. ............................ 445/25; 445/22; 445/23; 445/24; 445/26; 313/174; 313/504; 313/509
(58) Field of Search ........................... 445/25, 24, 23, 445/22, 50; 313/174, 220, 504, 509

(56) References Cited

U.S. PATENT DOCUMENTS

| 4,395,244 | A | * | 7/1983 | Glaser |
| 4,486,499 | A | | 12/1984 | Morimoto ................... 428/336 |
| 4,540,983 | A | | 9/1985 | Morimoto et al. .......... 340/772 |
| 4,708,678 | A | | 11/1987 | Tischer et al. ................ 445/24 |
| 4,849,674 | A | | 7/1989 | Cherry et al. ............... 313/509 |
| 5,273,475 | A | * | 12/1993 | Oshikawa |
| 5,788,551 | A | * | 8/1998 | Dynka et al. |
| 5,804,917 | A | | 9/1998 | Takahashi et al. .......... 313/504 |
| 5,846,110 | A | * | 12/1998 | Kanagu et al. |
| 6,010,384 | A | * | 1/2000 | Nishino et al. |

* cited by examiner

Primary Examiner—Dean A. Reichard
Assistant Examiner—Nguyen T. Ha
(74) Attorney, Agent, or Firm—Fish & Richardson P.C.

(57) ABSTRACT

The invention relates to a method for producing a structural component from at least one optoelectronic functional element and a glass pane, with the functional element being disposed in the region of a primary surface of the glass pane. This structural element is distinguished by the fact that the primary surface of the glass pane is connected to a frame such that the frame surrounds the edge surfaces of the functional element in the finished state of the composite element.

The invention further relates to a functional element that can be produced with the method.

20 Claims, 1 Drawing Sheet

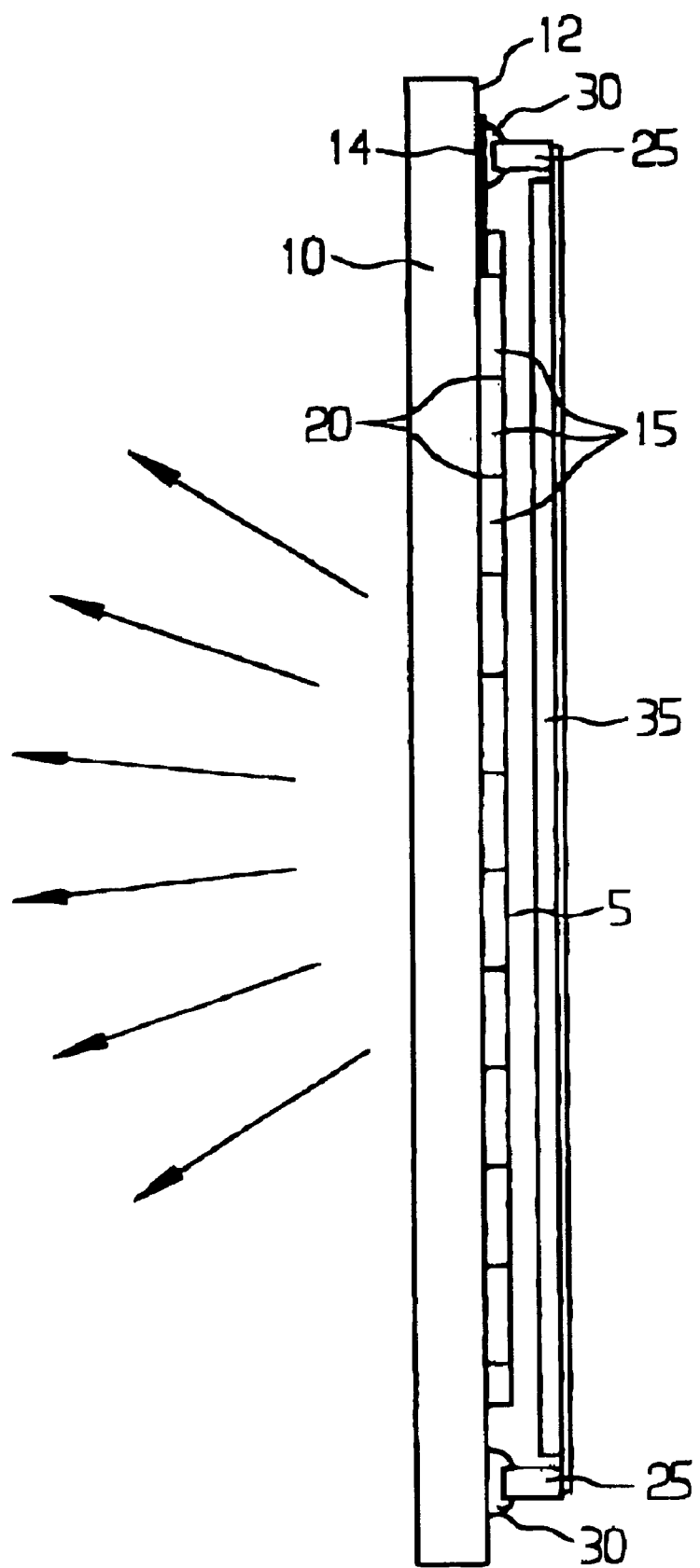

METHOD FOR PRODUCING A COMPONENT AND CORRESPONDING COMPONENT

TECHNICAL FIELD

The invention relates to a method for producing a structural element from at least one optoelectronic functional element and a glass pane, with the functional element being disposed in the region of an inside surface of the glass pane.

BACKGROUND

The invention further relates to a structural component comprising at least one optoelectronic functional element and a glass pane, with the optoelectronic functional element being disposed in the region of a primary surface of the glass pane.

In a known, generic method, the functional element is disposed between two parallel glass panes. The glass panes are then glued together. A problem occurring here, however, is that moisture diffuses into the empty space via the adhesive layer.

SUMMARY

It is the object of the invention to overcome the drawbacks of the prior art. In particular, the method to be provided is intended to be executed at the lowest-possible cost and implemented to produce a generic structural component in such a way that the functional element is as well-protected as possible against external influences.

In accordance with the invention, this object is accomplished in that the primary surface of the glass pane, which forms an inside surface in the finished structural element, is connected to a frame such that the frame surrounds the edge surfaces of the functional element in the finished state of the structural element.

The invention provides mounting a frame to the glass pane.

It is especially advantageous to execute the method of the invention such that the glass pane is first attached to the frame, and the functional element is then mounted in the region of the primary surface of the glass pane.

A notable advantage is that the conductor structure is mounted to the primary surface before the primary surface is secured to the frame.

The technology in accordance with the invention is particularly suitable if the functional element contains at least one organic light-emitting diode (OLED).

The materials making up the glass pane and the frame are advantageously selected such that their thermal expansion coefficients are extensively adapted to one another. An adaptation of this type can be effected, for example, through a change in the chemical composition of the glass, or a suitable selection of the frame material.

To this end, it is especially useful for the glass pane to be attached to the frame through soldering with a glass solder.

If, however, processing technology dictates the selection of a frame material that possesses a different expansion coefficient from that of the glass pane, which is the case, for example, for a metal frame, the connection between the glass pane and the frame must compensate various thermal expansions.

Glass solders are glasses whose especially low melting temperatures permit a glass-solder connection between the glass pane and the body to be attached thereto in this instance, the frame. The glass solder is selected to adequately flow and wet the surface at a temperature at which the glass pane still exhibits no interfering deformations. The temperature for the soldering process essentially corresponds to the transformation temperature of the glass solder.

It is crucial to adapt the glass solder to the thermal expansion of the connection partners, because the solder is the mechanically weaker connection partner. An advantageous execution of this method is distinguished by the fact that at least a portion of the glass solder is applied to the glass pane, and the frame is subsequently positioned relative to the glass pane.

The glass solder is applied to the glass pane through screen-printing, or dispensed in a line.

A further advantageous embodiment of the method is distinguished by the fact that at least a portion of the glass solder is applied to the frame, and the frame is subsequently positioned relative to the glass pane.

To provide better protection of the functional element with respect to external influences, it is advantageous to attach a lid to the frame. This is advisably effected through welding or soldering.

Further advantages, special features and modifications of the invention ensue from the dependent claims and the following description of a preferred exemplary embodiment illustrated in the attached drawing.

BRIEF DESCRIPTION OF THE DRAWING

FIG. 1 shows a cross-section of one structural component embodiment of the invention.

DETAILED DESCRIPTION

The drawing shows a cross-section through a structural component in accordance with the invention, having an optoelectronic functional element 5 and a glass pane 10. The functional element 5 is located on a primary surface 12 of the glass pane 10.

The functional element 5 is a display unit comprising a plurality of light-emitting diodes (LED), especially organic LEDs (OLEDs), disposed in a two-dimensional field.

The individual LEDs 15 include a plurality of functional layers, as described in, for example, the article by M. Schwoerer and H. v. Seggern: Electroluminescent Chromophores and Polymers for Organic LEDs and Displays, Siemens-Review Special; R & D, Herbst 1996, pp. 20 et seq.

The individual LEDs 15 form a display, with each LED corresponding to a respective pixel. A pixel is a two-dimensional picture element, such as a square.

The LEDs 15 comprise a plurality of functional layers, and are in direct contact with the glass pane 10 in the region of their primary surfaces. Connectors 20 are located between the LEDs 15.

A frame 25 that surrounds the functional element 5 on all side surfaces is disposed on the primary surface 12 of the glass pane 10. The frame comprises, for example, a suitable metal alloy or a ceramic material.

Glass solder 30 is located between the frame 25 and the primary surface 12 of the glass pane 10.

The frame 25 has a lid 35. The lid 35 comprises, for example, a suitable metal alloy.

The illustrated structural component is preferably produced as follows:

Conductor structures 14, e.g., in the form of conductor paths, are formed on the primary surface 12 of the glass pane 10 through the application of suitable materials. For this purpose, it is especially advantageous to use a cathode-sputtering method.

A glass solder, such as the commercially-available DM 2700 P, is then applied to the primary surface 12 of the glass pane 10.

As an alternative, it is possible to apply the glass solder to the frame 25 in regions intended for connecting the frame to the primary surface 12 of the glass pane 10. The advantage of applying the glass solder 30 to the primary surface 12 of the glass pane 10 is that this can be effected in a single work step, such as through screen-printing or dispensing of the glass solder in a line.

The frame 25 and the glass pane 10 are positioned relative to one another such that the frame is located directly above surface regions to which the glass solder has been applied. After the frame 25 has been positioned above the surface regions formed by the glass solder 30, the frame 25 is lowered onto these regions.

The glass solder is then warmed to its transformation temperature, which effects the soldering process. The glass solder used here has the particular advantage that it already flows at 350 degrees Celsius, which is a considerably low temperature for soldering procedures, and completely wets the surfaces to be connected. To ensure that the soldering process has been completed, it is advantageous for the soldering region to be maintained at 350 degrees Celsius for about 10 minutes during the actual soldering process.

In the soldering process, the glass solder 30 does not only wet the surfaces of the frame 25 facing the primary surface 12, but also lower regions of the side surfaces of the frame 25. This wetting process is detected through a visual check, and allows for the verification of the completion of the soldering process.

The functional element 5 is subsequently mounted to the primary surface 12 of the glass pane 10 inside the frame 25.

To effectively seal the functional element 5 against external influences, a lid 35 is then attached to the frame 25. This can be effected through soldering or welding, for example. Welding is particularly advantageous if the frame 25 and the lid 35 are both made of metal.

After the lid 35 has been attached to the frame 25, a final inspection is conducted and electrical connectors are mounted.

I claim:

1. A method for producing a component from at least one organic electroluminescent functional element (5) and a glass pane (10), wherein the organic electroluminescent functional element (5) is disposed in the region of a primary surface (12) of the glass pane (10), the method comprising:
   connecting the primary surface (12) of the glass pane (10) to a frame (25) such that the frame (25) surrounds the edge surfaces of the organic electroluminescent functional element in the finished state of the component and the frame (25) and glass pane (10) are connected with glass solder (30).

2. The method according to claim 1, wherein the glass pane (10) is first connected to the frame (25), and the organic electroluminescent functional element (5) is then mounted in the region of the primary surface (12) of the glass pane.

3. The method according to claim 1 or 2, further comprising mounting a conductor structure (14) to the primary surface (12) before the organic electroluminescent functional element (5) is disposed in the region of the primary surface of the glass pane.

4. The method according to claim 3, wherein the conductor structure (14) is mounted to the primary surface (12) before the primary surface is connected to the frame (25).

5. The method according to claim 1, wherein the organic electroluminescent functional element (5) is mounted to the primary surface (12) of the glass pane.

6. The method according to claim 1, wherein at least a portion of the glass solder (30) is applied to the glass pane (10), and the frame (25) is then positioned relative to the glass pane.

7. The method according to claim 1 or 6, wherein at least a portion of the glass solder (30) is applied to the frame (25), and the frame is then positioned relative to the glass pane (10).

8. The method according to claim 1, further comprising attaching a lid (35) to the frame (25).

9. The method according to claim 8, wherein the lid (35) is welded to the frame (25).

10. The method according to claim 8, wherein the lid (35) is soldered to the frame (25).

11. A method for producing a structural element, comprising:
   providing a glass pane;
   connecting a frame to the glass pane; and
   after connecting the frame to the glass pane, mounting at least one optoelectronic functional element on a primary surface of the glass pane such that the frame surrounds edge surfaces of an organic electroluminescent element.

12. A method for producing a structural element, comprising:
   providing a glass pane;
   mounting at least one optoelectronic functional element on a primary surface of the glass pane; and
   connecting a frame having sides surrounding an opening to the glass pane such that the frame surrounds edge surfaces of the functional element without covering a major surface of the functional element.

13. The method according to claim 12, wherein:
   the glass pane is first attached to the frame and the optoelectronic functional element is then mounted on the primary surface of the glass pane.

14. The method according to claim 12, further comprising:
   forming a conductor structure on the primary surface before mounting the optoelectronic functional element.

15. The method according to claim 12, wherein that the conductor structure is formed on the primary surface before connecting the frame to the primary surface.

16. The method according to claim 15, wherein connecting the frame to the glass pane includes applying at least a portion of the glass solder to the glass pane and positioning the frame relative to the glass pane.

17. The method according to claim 15, wherein connecting the frame to the glass pane includes applying at least a portion of the glass solder to the frame and positioning the frame relative to the glass pane.

18. The method according to claim 12, further comprising:
   attaching a lid to the frame.

19. The method according to claim 18, wherein attaching the lid includes welding the lid to the frame.

20. The method according to claim 19, wherein attaching the lid includes soldering the lid to the frame.

* * * * *